(12) United States Patent
Aali

(10) Patent No.: US 7,745,683 B2
(45) Date of Patent: Jun. 29, 2010

(54) DEFORMABLE AND CONFORMABLE WOUND PROTECTING APPARATUS AND ITS METHOD OF APPLICATION

(75) Inventor: Adel Aali, Irvine, CA (US)

(73) Assignee: Aalnex, Inc., Irvine, CA (US)

( * ) Notice: Subject to any disclaimer, the term of this patent is extended or adjusted under 35 U.S.C. 154(b) by 348 days.

(21) Appl. No.: 11/107,452

(22) Filed: Apr. 16, 2005

(65) Prior Publication Data

US 2006/0235347 A1 Oct. 19, 2006

(51) Int. Cl.
*A61F 13/00* (2006.01)
(52) U.S. Cl. .............................. 602/58; 602/41; 602/42; 128/888; 128/889
(58) Field of Classification Search ............... 602/3, 602/79, 41–59; 128/888, 889; D24/189
See application file for complete search history.

(56) References Cited

U.S. PATENT DOCUMENTS

| | | | | |
|---|---|---|---|---|
| 2,273,873 A | * | 2/1942 | Klein | ............... 128/888 |
| 2,305,289 A | | 12/1942 | Coburg | |
| 2,367,690 A | | 1/1945 | Purdy | |
| 2,443,140 A | | 6/1948 | Larsen | |
| 2,443,481 A | | 6/1948 | Sene | |
| 3,026,874 A | | 3/1962 | Stevens | ............... 604/305 |
| 3,334,626 A | | 8/1967 | Schimmel | |
| 4,023,569 A | | 5/1977 | Warnecke et al. | ............... 128/154 |
| 4,181,127 A | | 1/1980 | Linsky et al. | ............... 602/43 |
| 4,212,296 A | | 7/1980 | Schaar | ............... 602/42 |
| 4,252,120 A | | 2/1981 | Carpenter | |
| 4,726,364 A | | 2/1988 | Wylan | |
| 5,020,547 A | | 6/1991 | Strock | |
| 5,060,662 A | * | 10/1991 | Farnswoth, III | ............... 128/888 |
| 5,086,763 A | | 2/1992 | Hathman | |
| 5,101,837 A | | 4/1992 | Perrin | ............... 128/888 |
| 5,215,539 A | | 6/1993 | Schoolman | |
| 5,264,218 A | | 11/1993 | Rogozinski | |
| 5,356,372 A | | 10/1994 | Donovan et al. | ............... 602/58 |
| 5,376,067 A | | 12/1994 | Daneshvar | ............... 602/58 |
| 5,449,340 A | | 9/1995 | Tollini | |
| 5,456,660 A | | 10/1995 | Reich et al. | |
| 5,478,308 A | | 12/1995 | Cartmell | |
| 5,527,265 A | * | 6/1996 | McKeel | ............... 602/6 |
| 5,533,962 A | | 7/1996 | Peterman et al. | ............... 602/54 |

(Continued)

FOREIGN PATENT DOCUMENTS

WO WO9853778 * 12/1998

OTHER PUBLICATIONS

International Search Report for PCT/US06/14357, 2 pages (mailed Aug. 17, 2007).

(Continued)

*Primary Examiner*—Kim M Lewis
(74) *Attorney, Agent, or Firm*—Jones Day; Nicola A. Pisano; Jaime D. Choi

(57) ABSTRACT

A simple, versatile and easily applicable deformable wound protector apparatus for preventing foreign objects such as clothing and dressing from contacting the wound comprising a desirable length, a start and an end, and a lower and upper surface. The present invention may further include bridges and connectors to enhance its application. The deformable wound protector can conform to the specific contour and size of any wound and may be used with any dressing.

15 Claims, 12 Drawing Sheets

U.S. PATENT DOCUMENTS

| | | | |
|---|---|---|---|
| 5,603,946 A | 2/1997 | Constantine | |
| 5,695,456 A | 12/1997 | Cartmell et al. | |
| 5,702,356 A * | 12/1997 | Hathman | 602/41 |
| 5,817,145 A | 10/1998 | Augustine | |
| 5,843,011 A | 12/1998 | Lucas | |
| 5,885,237 A | 3/1999 | Kadash et al. | |
| 5,891,074 A | 4/1999 | Cesarczyk | 602/42 |
| 5,947,914 A | 9/1999 | Augustine | 602/2 |
| 5,954,680 A | 9/1999 | Augustine | 602/42 |
| 5,961,480 A | 10/1999 | Augustine | 602/41 |
| 5,964,721 A | 10/1999 | Augustine | 602/2 |
| 5,964,723 A | 10/1999 | Augustine | 602/42 |
| 5,968,163 A | 10/1999 | Narayan et al. | 712/204 |
| 6,000,403 A | 12/1999 | Cantwell | |
| 6,005,159 A | 12/1999 | Spier | 602/42 |
| 6,010,527 A | 1/2000 | Augustine et al. | 607/96 |
| 6,013,097 A | 1/2000 | Augustine et al. | 607/96 |
| 6,043,408 A | 3/2000 | Geng | |
| 6,045,518 A | 4/2000 | Augustine | 602/2 |
| 6,071,254 A | 6/2000 | Augustine | 602/2 |
| 6,071,304 A | 6/2000 | Augustine et al. | 607/96 |
| 6,080,189 A | 6/2000 | Augustine et al. | 607/96 |
| 6,093,160 A | 7/2000 | Augustine et al. | 602/2 |
| 6,095,922 A | 8/2000 | Friedrichsen et al. | 464/24 |
| 6,095,992 A | 8/2000 | Augustine | 602/2 |
| 6,110,197 A | 8/2000 | Augustine et al. | 607/108 |
| 6,113,561 A | 9/2000 | Augustine | 602/2 |
| 6,143,945 A | 11/2000 | Augustine et al. | 602/41 |
| 6,213,965 B1 | 4/2001 | Augustine et al. | 602/2 |
| 6,213,966 B1 | 4/2001 | Augustine | 602/2 |
| 6,217,535 B1 | 4/2001 | Augustine | 602/2 |
| 6,235,047 B1 | 5/2001 | Augustine et al. | 607/96 |
| 6,267,740 B1 | 7/2001 | Augustine et al. | 602/2 |
| 6,283,931 B1 | 9/2001 | Augustine | 602/2 |
| 6,293,917 B1 | 9/2001 | Augustine et al. | 602/2 |
| 6,320,093 B1 | 11/2001 | Augustine et al. | 602/41 |
| 6,323,386 B1 | 11/2001 | Stapf et al. | 602/41 |
| 6,406,448 B1 | 6/2002 | Augustine | 602/2 |
| 6,407,307 B1 | 6/2002 | Augustine | 602/42 |
| 6,419,651 B1 | 7/2002 | Augustine | 602/2 |
| 6,420,622 B1 | 7/2002 | Johnston et al. | 602/41 |
| 6,420,623 B2 | 7/2002 | Augustine et al. | 602/41 |
| 6,423,018 B1 | 7/2002 | Augustine | 602/2 |
| 6,426,066 B1 | 7/2002 | Najafi et al. | 424/78.04 |
| 6,436,063 B1 | 8/2002 | Augustine et al. | 602/2 |
| 6,440,156 B1 | 8/2002 | Augustine et al. | 607/96 |
| 6,458,109 B1 | 10/2002 | Henley et al. | |
| 6,465,708 B1 | 10/2002 | Augustine et al. | 602/42 |
| 6,468,295 B2 | 10/2002 | Augustine et al. | 607/96 |
| 6,485,506 B2 | 11/2002 | Augustine | 607/96 |
| 6,528,697 B1 | 3/2003 | Knutson | |
| 6,569,189 B1 | 5/2003 | Augustine et al. | 607/96 |
| 6,570,050 B2 | 5/2003 | Augustine | |
| 6,573,420 B2 | 6/2003 | Stapf et al. | 602/42 |
| 6,580,012 B1 | 6/2003 | Augustine et al. | 602/42 |
| 6,585,670 B2 | 7/2003 | Augustine et al. | 602/2 |
| 6,589,270 B2 | 7/2003 | Augustine | 607/96 |
| 6,605,051 B2 | 8/2003 | Augustine | 602/2 |
| 6,626,891 B2 | 9/2003 | Ohmstede | |
| 6,641,601 B1 | 11/2003 | Augustine et al. | 607/96 |
| 6,653,520 B1 | 11/2003 | Mouton | 602/45 |
| 6,685,681 B2 | 2/2004 | Lockwood et al. | |
| 6,716,235 B2 | 4/2004 | Augustine et al. | 607/96 |
| 6,840,915 B2 | 1/2005 | Augustine | 602/2 |
| 6,921,374 B2 | 7/2005 | Augustine | 602/2 |
| 6,960,181 B2 | 11/2005 | Stevens | |
| 6,974,428 B2 | 12/2005 | Knutson et al. | 602/2 |
| 7,012,170 B1 | 3/2006 | Tomaioulo | |
| 7,074,982 B2 * | 7/2006 | Knutson et al. | 602/42 |
| 7,112,712 B1 | 9/2006 | Ancell | |
| 7,118,545 B2 | 10/2006 | Boyde | 602/79 |
| 7,122,046 B2 | 10/2006 | Augustine et al. | 607/96 |
| 7,122,712 B2 | 10/2006 | Lutri et al. | 602/43 |
| 7,135,606 B1 | 11/2006 | Dozier et al. | 602/57 |
| 7,176,343 B2 | 2/2007 | Schlussel | |
| 7,183,454 B1 | 2/2007 | Rosenberg | |
| 2002/0007136 A1 | 1/2002 | Narula et al. | 602/46 |
| 2002/0026133 A1 | 2/2002 | Augustine et al. | 607/2 |
| 2002/0029010 A1 | 3/2002 | Augustine et al. | 602/41 |
| 2003/0088201 A1 * | 5/2003 | Darcey | 602/44 |
| 2004/0249328 A1 | 12/2004 | Linnane et al. | 602/43 |
| 2005/0004500 A1 | 1/2005 | Rosser et al. | |
| 2005/0010153 A1 | 1/2005 | Lockwood et al. | |
| 2005/0070835 A1 | 3/2005 | Joshi | |
| 2005/0107732 A1 | 5/2005 | Boyde | |
| 2005/0113731 A1 | 5/2005 | Qvist | 602/48 |
| 2005/0148921 A1 | 7/2005 | Hsu | 602/48 |
| 2005/0222528 A1 | 10/2005 | Weston | |
| 2006/0064049 A1 | 3/2006 | Marcussen | 602/42 |
| 2006/0116620 A1 | 6/2006 | Oyaski | |
| 2006/0189909 A1 | 8/2006 | Hurley et al. | 602/41 |
| 2006/0235347 A1 | 10/2006 | Aali | |
| 2006/0253089 A1 | 11/2006 | Lin | 604/301 |
| 2007/0142757 A1 | 6/2007 | Aali | |
| 2007/0142761 A1 | 6/2007 | Aali | |
| 2007/0161937 A1 | 7/2007 | Aali | |
| 2007/0161938 A1 | 7/2007 | Aali | |
| 2007/0191754 A1 | 8/2007 | Aali | |

OTHER PUBLICATIONS

USPTO Notice of Allowance for U.S. Appl. No. 11/409,364, 7 pages (mailed Jul. 10, 2009).
USPTO Final Office Action for U.S. Appl. No. 11/409,364, 9 pages (mailed Mar. 10, 2009).
USPTO Non-Final Office Action for U.S. Appl. No. 11/409,364, 7 pages (mailed May 22, 2008).
USPTO Advisory Action for U.S. Appl. No. 11/409,364, 3 pages (mailed Apr. 8, 2008).
USPTO Final Office Action for U.S. Appl. No. 11/409,364, 7 pages (mailed Nov. 30, 2007).
USPTO Non-Final Office Action for U.S. Appl. No. 11/409,364, 7 pages (mailed May 31, 2007).
USPTO Non-Final Office Action for U.S. Appl. No. 11/303,463, 10 pages (mailed Mar. 17, 2009).
USPTO Final Office Action for U.S. Appl. No. 11/303,463, 9 pages (mailed Dec. 26, 2008).
USPTO Non-Final Office Action for U.S. Appl. No. 11/303,463, 11 pages (mailed Mar. 18, 2008).
USPTO Non-Final Office Action for U.S. Appl. No. 11/707,464, 11 pages (mailed Apr. 14, 2009).
USPTO Non-Final Office Action for U.S. Appl. No. 11/707,464, 8 pages (mailed Jun. 27, 2008).
USPTO Notice of Allowance for U.S. Appl. No. 11/303,155, 5 pages (mailed Jun. 12, 2009).
USPTO Non-Final Office Action for U.S. Appl. No. 11/303,155, 7 pages (mailed Jan. 8, 2009).
USPTO Non-Final Office Action for U.S. Appl. No. 11/303,155, 9 pages (mailed Jul. 14, 2008).
USPTO Final Office Action for U.S. Appl. No. 11/441,702, 12 pages (mailed Apr. 10, 2009).
USPTO Non-Final Office Action for U.S. Appl. No. 11/441,702, 8 pages (mailed Jun. 26, 2008).
USPTO Non-Final Office Action for U.S. Appl. No. 11/441,702, 9 pages (mailed May 1, 2007).

* cited by examiner

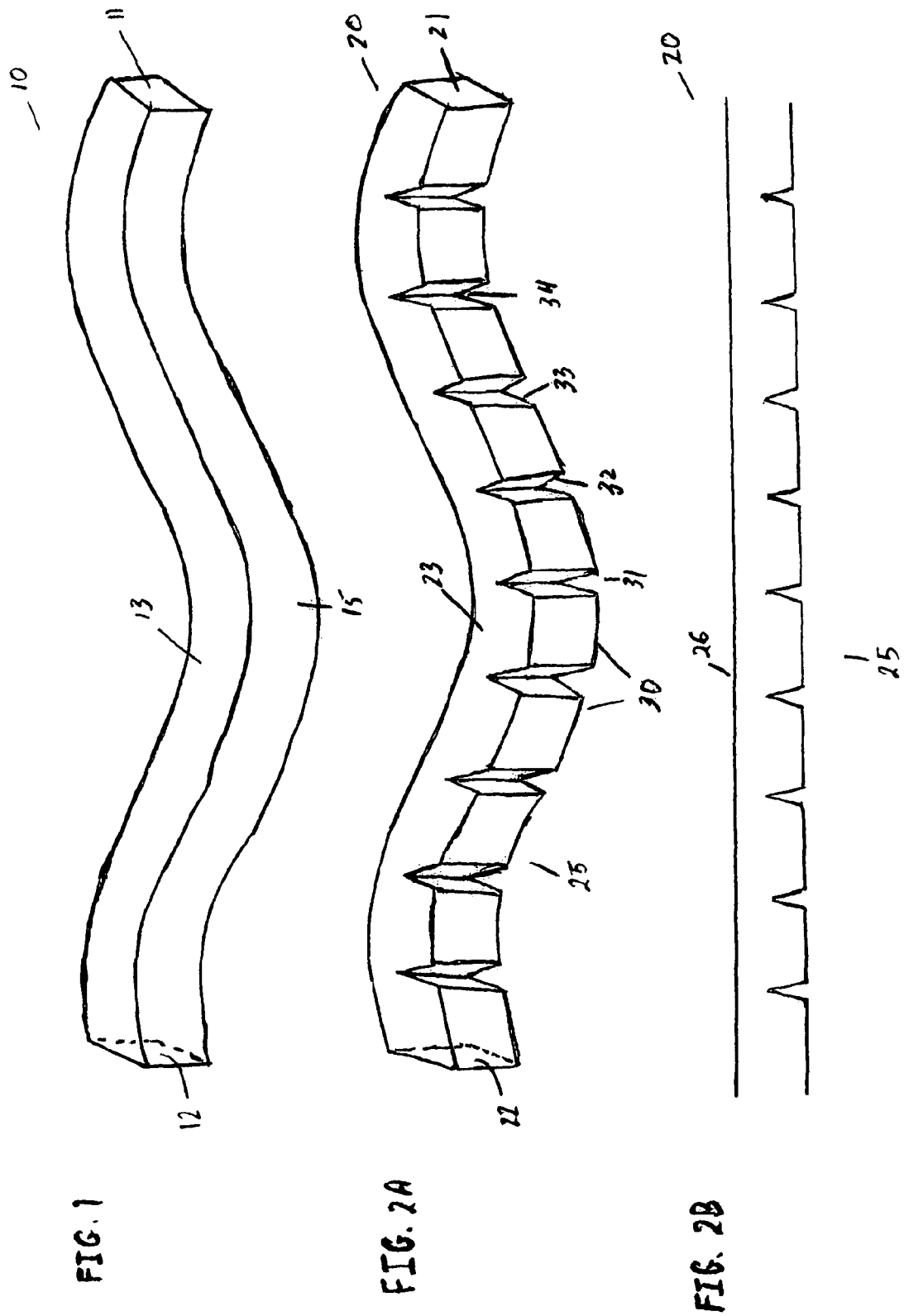

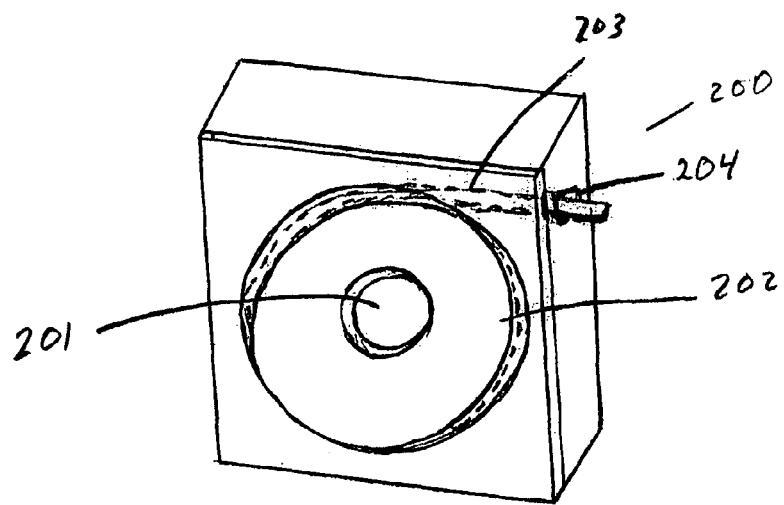
FIG. 15A
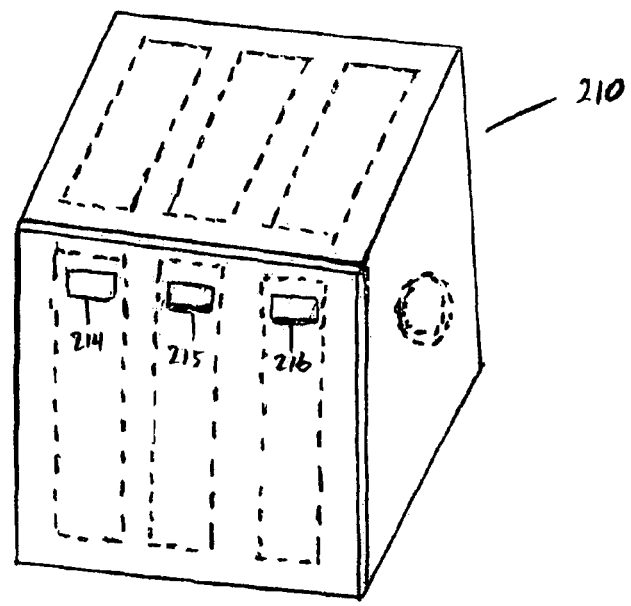
FIG. 15B
FIG. 15C
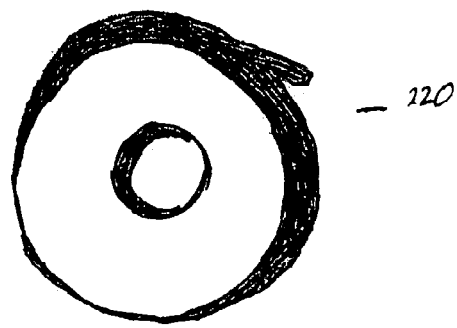

DEFORMABLE AND CONFORMABLE WOUND PROTECTING APPARATUS AND ITS METHOD OF APPLICATION

FIELD OF THE INVENTION

The present invention is an apparatus and method for use in wound care management and may be used to protect the wound from injurious contact with clothing, dressing and other such foreign objects. The present invention may also be used to relieve pressure from wounds such as pressure ulcers.

BACKGROUND OF THE INVENTION

Wounds occur when the integrity of any tissue is compromised, affecting one or more layers of skin. Wounds may be caused by an act, surgical procedure, an infectious disease or an underlying condition. Examples of open wounds include punctures, abrasions, cuts, lacerations and burns. Chronic wounds are also common ailments and include pressure ulcers, diabetic ulcers, arterial ulcers, venous ulcers or combination of all the above. Despite much progress made in the wound care industry, an efficient and effective method and apparatus for protecting the wound from injurious contacts is not readily available.

Injurious contacts with foreign objects may be caused from various sources, ranging from brushing of clothing or bed sheets to fresh, uncovered wounds to adherence of wound dressing to the wound. The latter issue, referred to here as the sticking issue, leads to deleterious consequences for the patient. This problem is particularly exacerbated when wounds are left unattended for a substantial period. It is reported that in certain circumstances patients are administered morphine to withstand the pain caused form dressing removal, especially with wounds having a large surface area. Equally important, tearing of skin graft, newly formed cells or scab adhered to dressing disrupts the healing process.

The main reason for covering the wound with dressing is to prevent contamination and resulting infection. Wounds may also be covered for other reasons, including retaining moisture and absorption of exudate. Wound covering has traditionally consisted of application of dressings that are in direct contact with the wound. When directly applied on the wound, dressings adhere and mechanically anchor to wound surface, which may include diffused wound fluid, skin graft, new epidermal cells forming over the wound or the scabby covering of the wound.

The sticking issue has traditionally been addressed by soaking the wound and the dressing adhering to it in water for sometime to soften the scab and make removal easier. Another method is the application of antibiotic ointments, such as polymyxin B sulfate or bacitracin, to keep the bandage from sticking to the wound. These methods, however, have not sufficiently addressed the sticking issue. As can be appreciated by health care professionals, soaking in water or application of ointments are not always practicable or recommended.

To better address the sticking issue the medical industry has developed "non-stick" dressings such as Telfa® and Xeroform®. Non-stick, however, is a relative term. Non-stick dressings merely stick less than their traditional counterparts, e.g., cotton gauze. Another problem with these dressings is that their cost is prohibitive for use on wounds requiring constant change of dressing.

"Non-contact" dressings have also been invented to address the sticking issue. These dressings are primarily designed in the shape of an inverted cup or a raised bandage. The general idea is that the space within the cup or raised bandage covers the wound, but does not come in contact with it. Such dressings are described in, e.g., U.S. Pat. Nos. 2,367,690; 2,443,140; 2,443,481; 3,334,626; 4,726,364; 5,817,145; 6,528,697; and 6,570,050.

Similar to the traditional and "non-stick" dressings described above, "non-contact" dressings also fail to efficiently and effectively protect the wound from contact, including addressing the sticking issue. First, they cannot be sufficiently deformed for the specific contours of different wounds, such as a narrow, long laceration. Second, they are designed in specific sizes that are not necessarily the desirable size for the wound.

U.S. Pat. No. 2,443,481 to Sene attempts to address this matter via an isolator having slots cut into its side wall, providing independent tongues in a deformable arrangement that "are easy to displace by reason of their flexibility and may follow readily the outline of the wound to be treated . . . . " See Sene at Col. 3:19-30, FIG. 3. More recently, U.S. Pat. No. 6,528,697 to Knutson attempted to address this problem in a similar manner, by providing a standoff with notches on its side wall that may be deformed or bent to the size and for the contours of the wound. See Knutson at Col. 6: 17-60, FIGS. 7A-7D. No matter how deformable or flexible their "tongues" or "notches" may be, both Sene and Knutson are limited in how much and how well they can follow the outline of the wound. In addition, their deformability and flexibility can only expand their size to a finite amount. Thus, they are inherently limited in size and constrained in their ability to specifically conform to the contour of the wound. Furthermore, the slots or notches cut in their side walls allow for diffusion of exudate from the wound on to adjacent areas. These references address this latter issue by adding more parts to their apparatus, which in turn makes them more complex, difficult to use and cost prohibitive.

Knutson also attempts to addresses the size and deformability issue by bundling several size dressings in one package. See Knutson at FIGS. 5 and 6. Aside from the fact that the myriad of sizes offered may still fail to provide the appropriate size for the wound, with such bundled package many dressing sizes in the package may never be used—a waste of financial resources.

Aside from their size limitation and lack of deformability, the prior art "non-contact" dressings have other drawbacks. Their complicated design makes their costs a prohibitive factor and application difficult. In addition, with wounds for which the purpose of a non-contact bandage is primarily protection from physical contact, including prevention of dressing from adhering to the wound bed, the prior art non-contact dressings are unnecessarily too complicated and an overkill. Moreover, whether several dressing sizes bundled together, or more than one dressing is in use, the prior art non-contact dressings are unable to address wounds on body segments with small surface areas. For example, using a large square, oval or circular bandage to cover a large, narrow and oddly shaped laceration on the forearm or shin is impractical. The same is true for the face and neck regions. Similarly, due to their specific shape and size, the non-contact dressings of prior art are not able to address wounds located in joints, such as elbows or knees.

Thus, the need exists for a wound apparatus and application method that more effectively protects the wound from injuries caused by contact, including addressing the problem of dressing adhering to wound surface.

SUMMARY OF THE INVENTION

The present invention is a simple, versatile, inexpensive and readily applicable apparatus and method for wound protection. It is comprised of a deformable wound protecting apparatus that can conform to the specific contour and size of any wound and be used with any dressing. The present invention prevents foreign objects such as clothing, dressings and other such items from contacting the wound. A simple cotton gauze dressing may be placed on the present invention to completely protect the wound from harmful contact with any object.

The deformable member of the present invention may be constructed from material capable of deformation in the X, Y and Z axis. Silicone is one example of such material, as it is both rigid and deformable. Polymers such as polypropelene, polyethylene and polyurethane may also be used to form a deformable, and yet rigid wound protector. Depending on its specific use, secondary features of the present invention may include impermeability to water, bacteria and air, and absorption of fluids exuding from the wound bed. The present invention may also have a moisture vapor transmission rate (MVTR). In the preferred embodiment of the present invention, polyurethane foam is used for its ability to absorb exudate. The present invention may be constructed from other material available in the art, using development and manufacturing methods understood by those of ordinary skill in the art.

The preferred embodiment of the present invention is a wound protector that adheres to the skin surrounding the wound via adhesive applied to its surface in contact with skin. Medical grade, hypo-allergenic, e.g., rubber-based, acrylic, vinyl ether and hydrocolloid pressure-sensitive are examples of adhesives that may be used with the present invention. For their obvious advantages, adhesives that adhere to body hair less than their conventional counterparts are preferred.

Adhesives may also be added to the surface of the present invention not in contact with skin so that it adheres to the dressing. In another embodiment, no adhesive is applied to the wound protector, and it stays in place by the pressure applied form the dressing wrapped around the wound.

The deformable member of the present invention may be provided in many different container embodiments. For example, the deformable member can be wound around a reel and placed in a dispenser that can be efficiently stored. When needed, the deformable member of the present invention may be pulled out of the dispenser, and cut to desired lengths. The deformable member is placed around the wound, creating a boundary and providing a plane higher than that of the wound for the dressing to rest on. Alternatively, the present invention may be supplied in a sheet form and cut to the desired length and width. Moreover, the deformable member may be pre-packaged in several long strips with various or equal widths that can be cut to desirable lengths.

The present inventions has many advantages over the prior art. It is fully deformable to conform to specific contours of any wound. It can be cut to a desirable length to follow the perimeter of any wound, regardless of shape and size. In addition, it can be made of inexpensive and yet effective material. Equally important, the dressing used in conjunction with the present invention can range from the inexpensive, commonly used cotton gauze to the more costly and sophisticated dressings, including those constructed from transparent and several layered material with qualities such as exudate absorption, air and bacteria impermeability and moisture permeability, just to name a few. With the present invention health care professionals can mix and match various dressings without restriction to complex and/or costly non-contact dressings.

The present invention can be conveniently stored in various compact dispensers, requiring minimal storage. Moreover, it can be cut into various desirable lengths and logistically placed around the wound to manipulate the proper positioning of dressing in difficult areas, such as joints, face and neck.

It is therefore an object of the present invention to provide an apparatus with sufficient rigidity to prevent injurious contacts to the wound, including those caused by dressing adhering to the wound surface. It is another object of the present invention to provide a deformable apparatus that conforms to the contour of the wound. It is a further object of the present invention to provide an apparatus for protection of wounds regardless of their size. It is also another object of the present invention to allow for application of dressings to joints, such as knee and elbow, without contacting the wound. Moreover, it is another object of the present invention to provide an apparatus that allows for versatile use of various dressings.

Further objects and advantages of the present invention will become apparent from a consideration of the drawings and ensuing descriptions.

BRIEF DESCRIPTION OF THE DRAWINGS

FIG. 1 is a partial perspective view of the preferred embodiment of the deformable member of the present invention.

FIG. 2A is a perspective view of an alternative embodiment of the deformable member of the present invention. FIG. 2B is a top view of the same embodiment, demonstrating differences between its proximal and distal sides.

FIGS. 15A, 15B and 15C depict examples of various dispensers that may be used with the present invention.

DETAILED DESCRIPTION OF THE INVENTION

Figure 3:
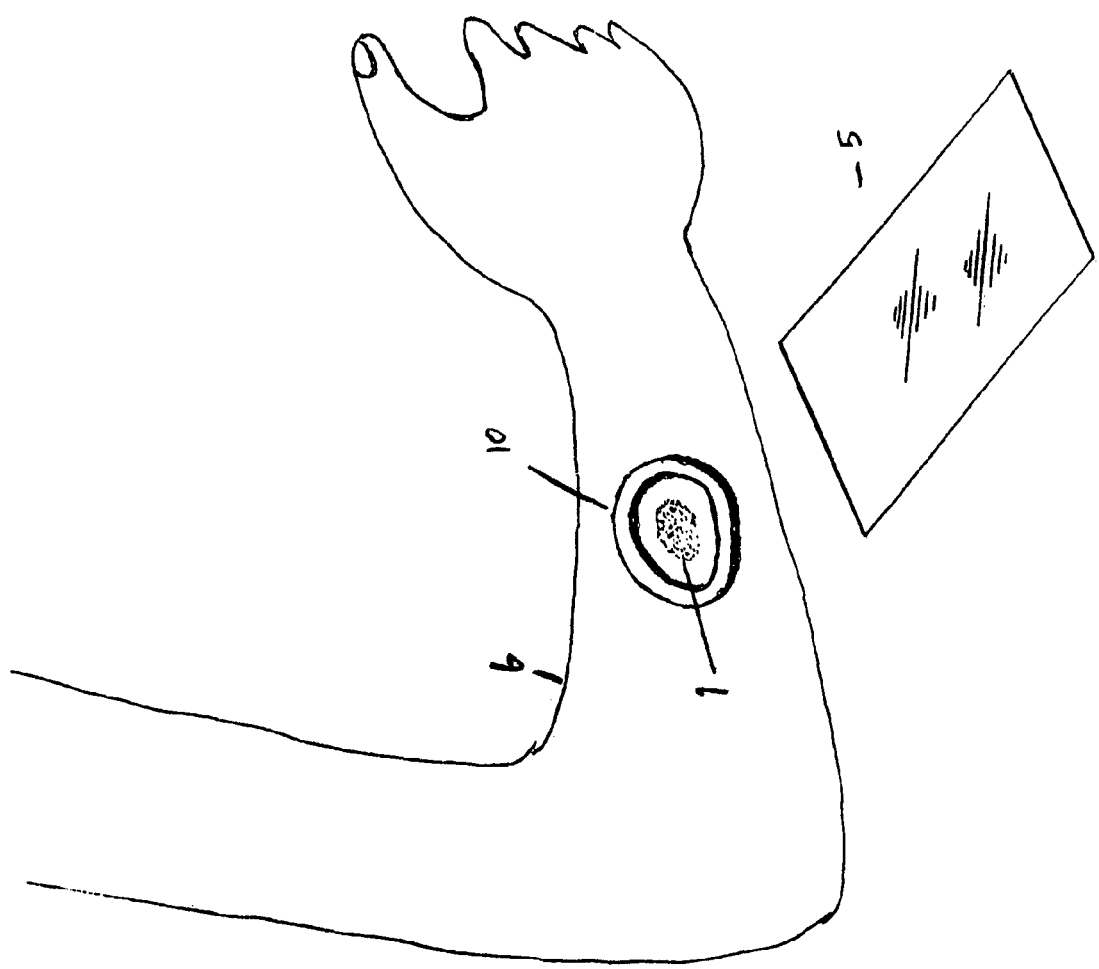
FIG. 3 depicts the preferred embodiment of the present invention in use with a small wound on the forearm.

FIG. 1 illustrates the preferred embodiment of the deformable member of the present invention. A deformable member 10 is depicted in a curved formation to demonstrate its deformability, which allows it to conform to specific contour of the wound. Examples of various shaped wounds and application of the present invention to those wounds are depicted in FIGS. 3-6 and 11.

Deformable member 10 is comprised of distal side 15 facing away from the wound and proximal side 16 (not shown) facing the wound. Deformable member 10 is further comprised of upper surface 13 not in contact with skin surrounding the wound, and lower surface 14 (not shown) in contact with said skin. Various adhesives may be applied to lower surface 14 or upper surface 13 or preferably to both. The adhesive material may be covered by a strip or a film that can be peeled off at the time of use. When applied on surface 14, adhesives will adhere the deformable member 10 to skin surrounding the wound. When applied to surface 13, adhesives will adhere the deformable member 10 to dressing used in conjunction with it.

It should be noted that in certain circumstances health care professionals may recommend the airing of the wound, i.e., not covering the wound with any dressing. As such, the present invention may be used to simply protect the wound from physical contact with other foreign objects, e.g., clothing or bed sheets.

For patients allergic to medically approved adhesives, the deformable member can be provided without the application of adhesive or, alternatively, with application of adhesive only to surface 13. In such circumstances, health care professionals must ensure to place dressing on deformable member 10 with sufficient and appropriate pressure so to keep deformable member 10 in place.

Figure 12:
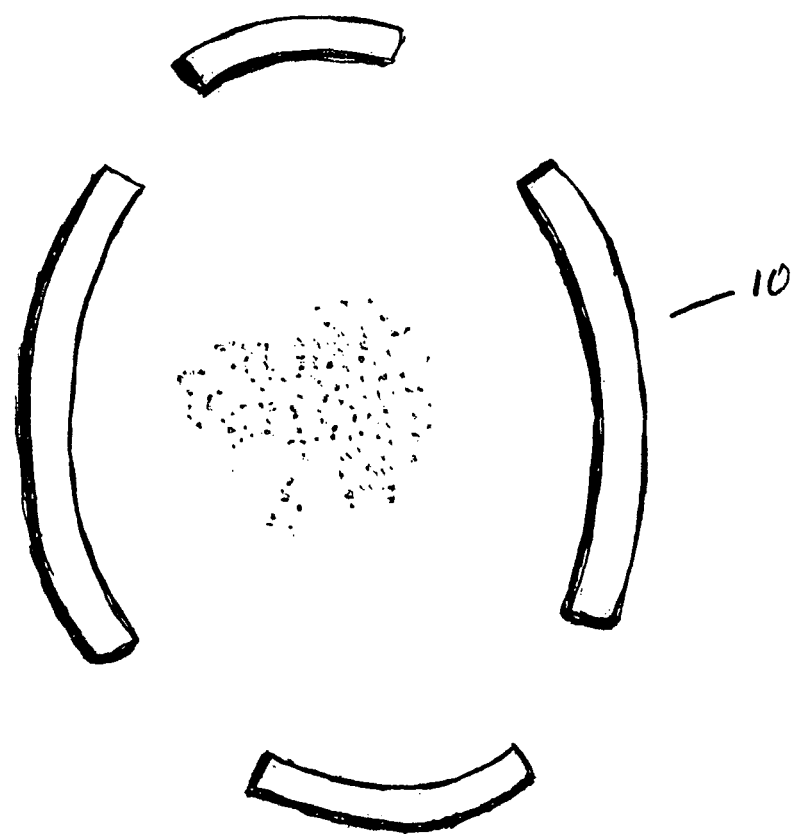
FIG. 12 depicts the deformable member of the present invention as it is used in various desirable lengths.

Regardless of its chosen size, deformable member 10 is always comprised of start 11 and end 12. When positioned around a wound, start 11 and end 12 meet to completely circumscribe the wound. This is shown in FIGS. 3-6. However, as depicted in FIG. 12, deformable member 10 does not always circumscribe the wound. For wounds positioned in logistically difficult body extremities, such as the elbow and knee, it may be desirable to cut the deformable member to several equal or varying desirable lengths and logistically position them around the wound. Such manipulation can allow positioning of the dressing without contacting the wound. As manifested in FIG. 12, start 11 and end 12 are not in contact.

FIGS. 3-6 and FIG. 12 demonstrate another advantage and application of the present invention. As depicted in FIG. 12, the deformable member can be cut in various or equal desirable lengths and logistically placed around a wound. In addition to protecting the wound from contact, such application is useful for relieving pressure from pressure ulcers.

FIGS. 2A and 2B depict deformable member 20, which is another embodiment of the deformable member of the present invention. Deformable member 20 is different than deformable member 10 in that it consists of a plurality of grooves 31, positioned in its distal side 25. As shown in FIG. 2B, proximal side 26 of deformable member 20 does not have grooves 31, and therefore does not mirror side 25. The purpose of grooves 31 is to provide flexibility for material that cannot otherwise be constructed with sufficient flexibility to allow appropriate deformability for purposes of this invention. Grooves 31 may be cut into deformable member 20 using standard techniques known in the art. As depicted in FIG. 2B, groove 31 consists of an angled side 32 and an angled side 33, both having proximal and distal portions, where their proximal portions meet at a center 34. Each groove 31 is separated by a middle section 30. It should be appreciated that FIG. 2B provides only an example of one embodiment of groove 31. Many other embodiments are possible, including one in which sides 31 and 32 are curved instead of angled.

FIG. 3 depicts the application of the deformable member of the present invention to wound 1, which is situated on forearm 6. Deformable member 10 is shown for drawing convenience and it should be appreciated that deformable member 20 can also used for wound 1 and could have been depicted in FIG. 3. Start 11 and end 12 are not visible in FIG. 3, as well as FIGS. 4-6 and 11, because deformable member 10 has fully circumscribed wound 1 and start 11 and end 12 are in contact. When dressing 5 is used in conjunction with the present invention, deformable member 10 prevents it from contacting wound 1 by creating a plane higher than that of the wound for the dressing to rest on.

As briefly described above, dressing 5 may be any dressing available to health care practitioner appropriate for treatment of wound 1. Dressing 5 may be comprised of adhesives along its longitudinal and/or its transverse lengths, so to facilitate its adherence to skin surrounding the wound and the present invention. Alternatively, dressing 5 may be wrapped around the arm or other body parts on which wound 1 is situated.

Figure 4:
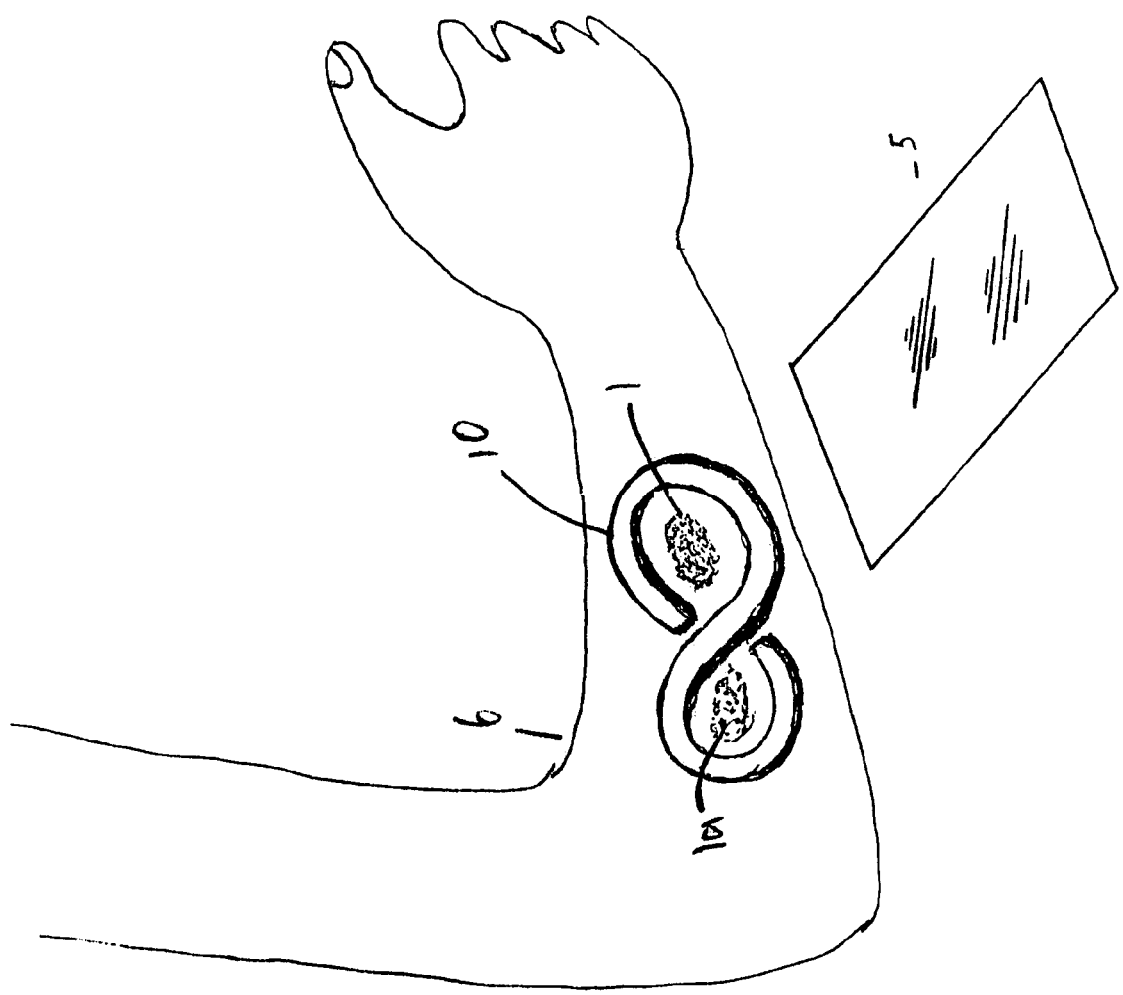
FIG. 4 depicts the preferred embodiment of the present invention in use with two proximately located wounds on the forearm.

FIG. 4 depicts deformable member 10 as it is used in conjunction with two proximately located wounds 1 and 1a on forearm 6. Start 11 and end 12 are not in contact as deformable member 10 is wrapped around wounds 1 and 1a in the shape of a figure eight. The space between start 11 and end 12 and side 15 and side 16 of deformable member 10 in FIG. 4 is for illustration purposes only. To prevent exudate from flowing away from wounds 1 and 1a, start 11 and end 12 would contact side 15 or side 16.

Figure 5:
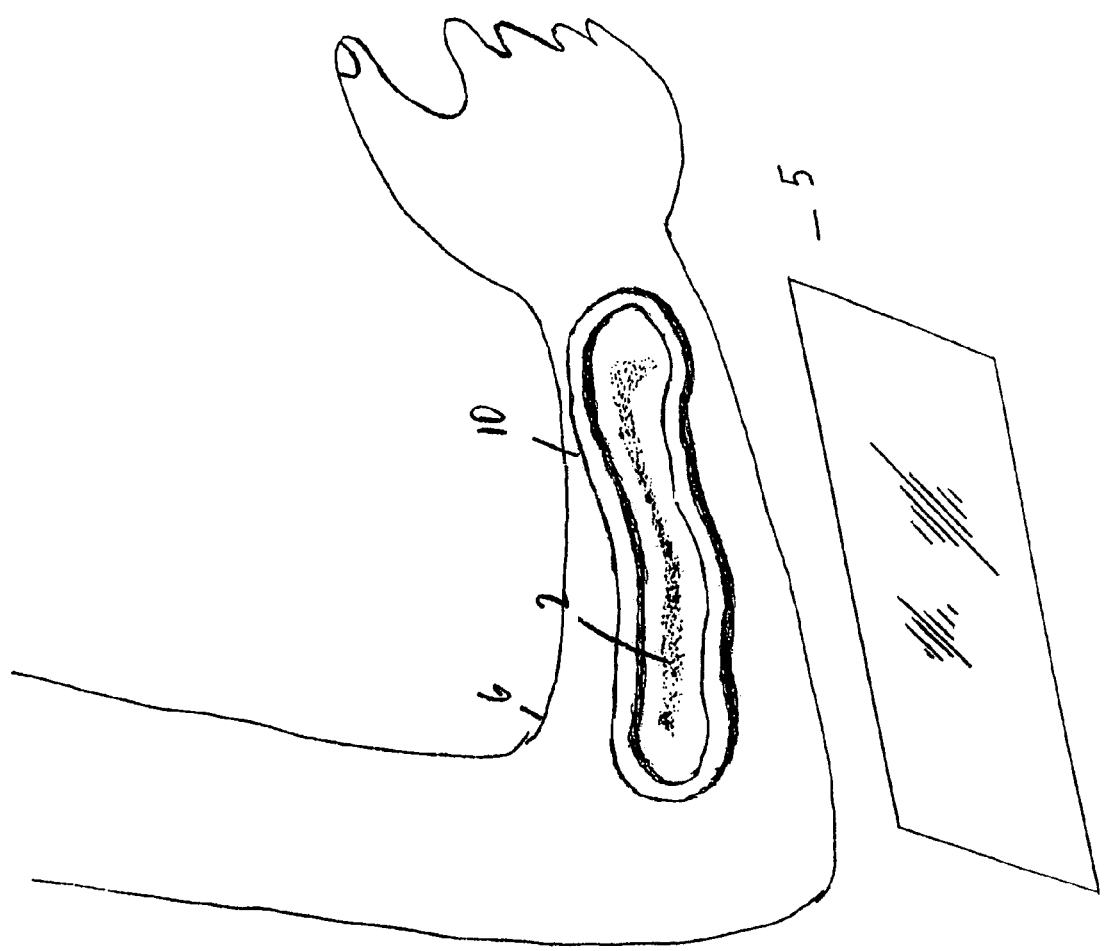
FIG. 5 depicts the preferred embodiment of the present invention in use with a long, oddly shaped laceration on the forearm.

FIG. 5 depicts deformable member 10 as it is used in conjunction with wound 2, which is a long, narrow, oddly shaped laceration. Other non-contact bandages are not conveniently able to circumscribe the length and shape of wound 2. As discussed above, more than one non-contact bandage may have to be used. With the present invention, however, health care professional may continue to use dressing 5 with wound 2. Dressing 5 may be applied along its length, width, or in tandem with another dressing 5 or other dressings. The essential point is that health care professionals are able to protect this wound without resort to another size dressing or another non-contact bandage.

Figure 6:
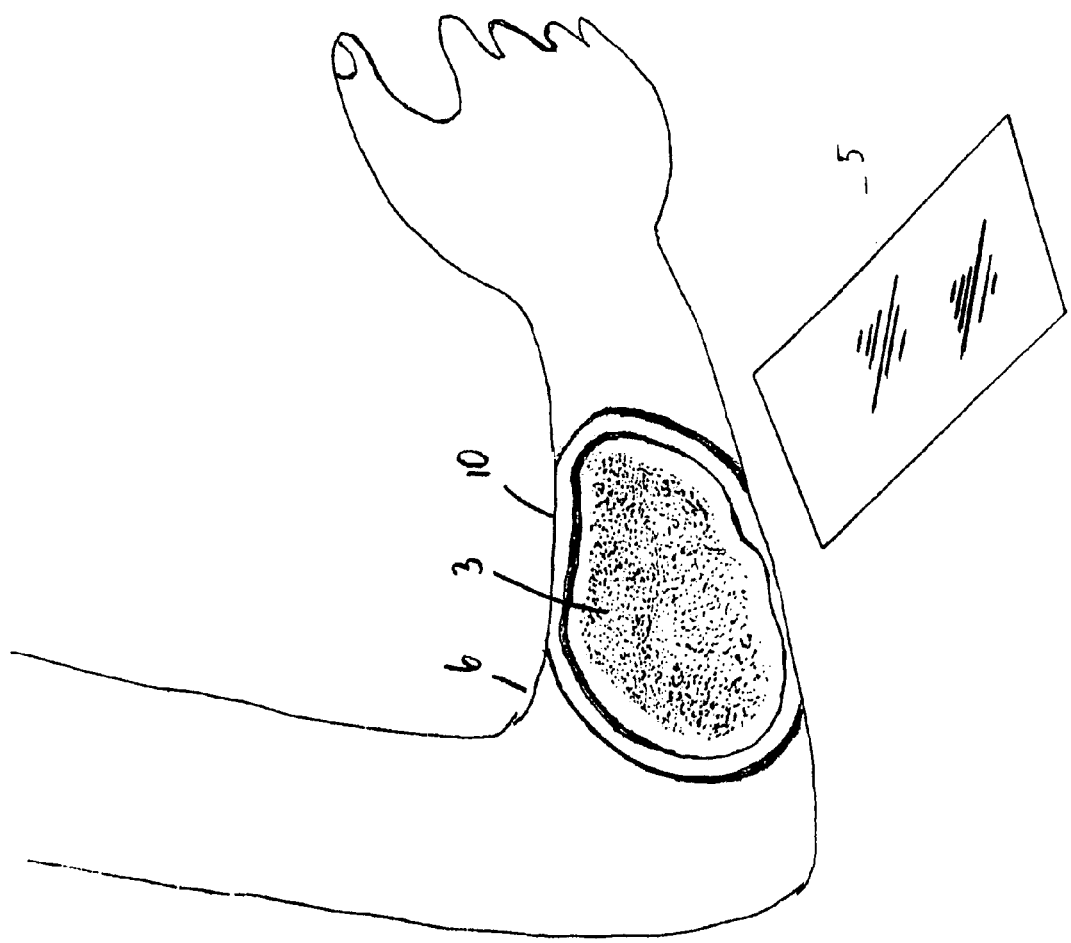
FIG. 6 depicts the preferred embodiment of the present invention in use with a large wound on the forearm.

FIG. 6 depicts deformable member 10 as it is used with wound 3, which is a much larger wound than wounds 1 and 2. As shown, dressing 5 can still be used for wound 3, whether it is applied at its width or length, or whether it is used in a tandem arrangement with more than one dressing 5 or another type of dressing. Again, FIG. 6 conveys the versatile application of the present invention to wounds of various shapes and sizes.

Figure 7:
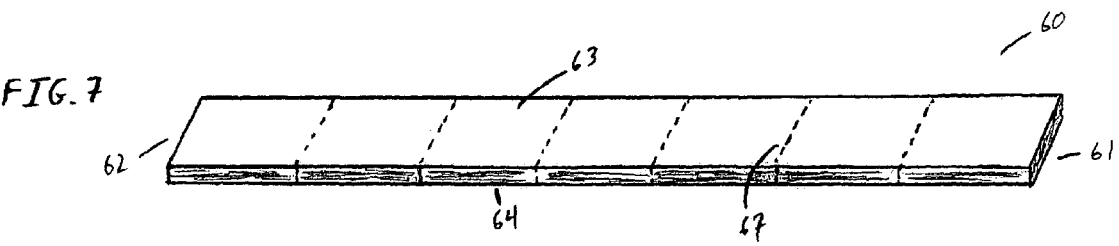
FIGS. 7-9 depict various bridge members of the present invention that may be used in conjunction with the deformable member.
Figure 8:
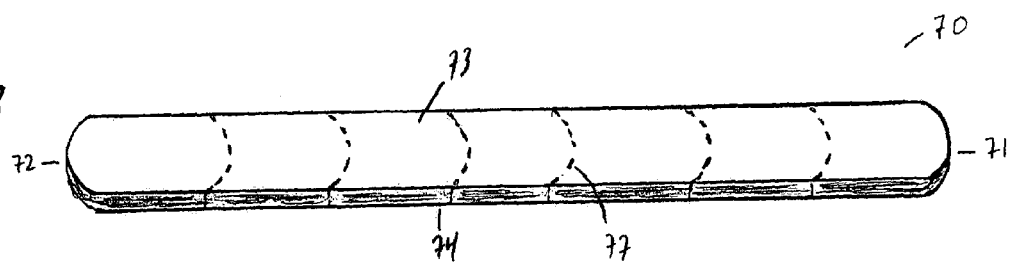
Figure 9:
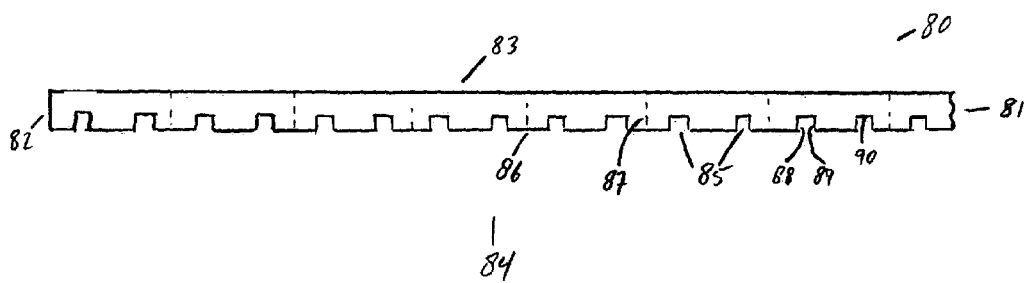
Figure 11:
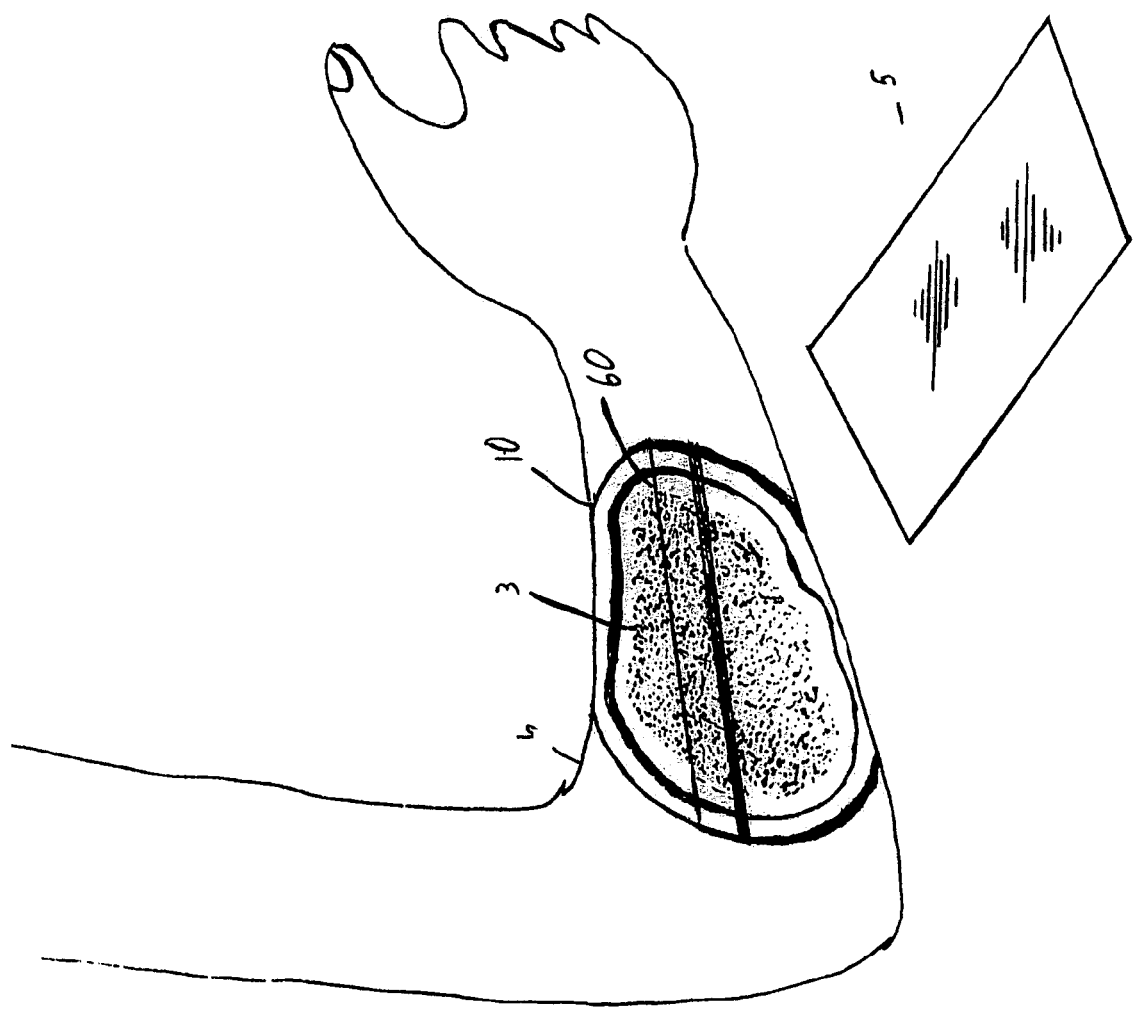
FIG. 11 depicts the application of the preferred embodiment of the bridge member on the deformable member, as used on a large wound on the forearm.

FIGS. 7-9 depict various bridge members of the present invention for use with the deformable member. The bridge member may be used in wounds with large surface areas, such as wound 3 depicted in FIG. 11. It is anticipated that for certain large wounds the dressing used with the deformable member 10 may sink due to various reasons, including loss of tautness or pressure. Positioning of one or more bridge members on deformable member 10, as depicted in FIG. 11, is intended to prevent the dressing from sinking and touching wound 3.

The bridge member can have various shapes, such as bridge member 60 with a start 61 and an end 62 with straight edges, or bridge member 70 with a start 71 and an end 72 with curved edges. The precise shape of the bridge is unimportant, and it should be appreciated that various shapes will serve the intended purposes of the present invention. The bridge may be constructed from inexpensive medical grade rigid plastic polymers, or wood particularly condition for medical use. Such material should be structurally designed to allow breakage at perforated portions 67, 77 and 87 along the length of the bridge. Medical grade adhesive can be applied to proximal surface 64 and proximal surface 74, as that surface will come in contact with deformable member 10.

A thin layer of film or strip removable at time of use may cover the adhesive. The thin layer of film or strip should be perforated at the same locations as perforations 67 and 77. In another embodiment, bridge members 60 and 70 may have adhesive on both sides to further secure them by adhering not only to deformable member 10, but also to dressing 5 along their distal surface 63 and surface 73. In this embodiment, a thin layer of film covering the adhesive is applied to both sides of the bridge member. Alternatively, bridge members 60 and 70 may have no adhesive at all. In such circumstance, they attach to deformable member 10 by virtue of adhesive in place on deformable member 10.

FIG. 9 depicts bridge member 80, which is another embodiment of the bridge member of the present invention. Bridge 80 is comprised of a plurality of indentations 85, each indentation 85 separated from the adjacent indentation 85 by a flat section 86. Each indentation 85 is comprised of a bed 90, a side 88 and a side 89. Width of bed 90 is slightly larger than width of surface 13 of deformable member 10.

Figure 10:
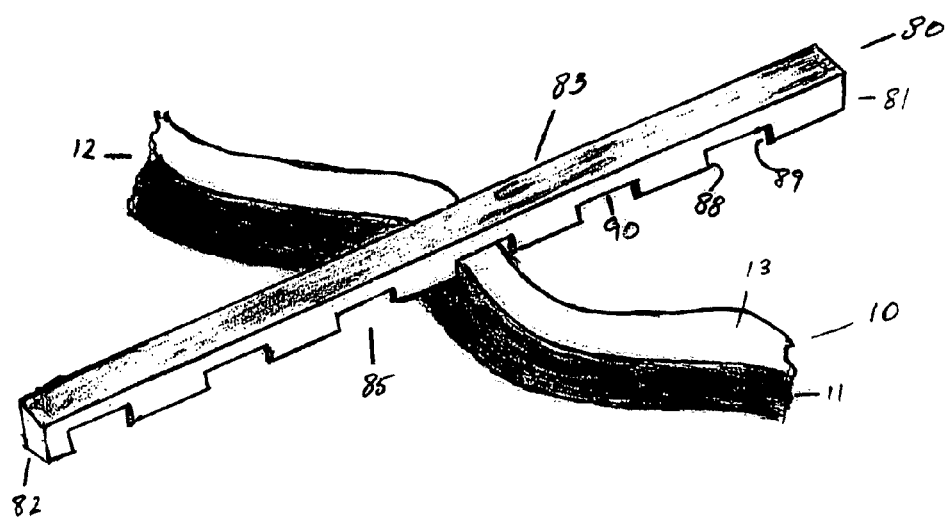
FIG. 10 depicts the use of one embodiment of the bridge member with the deformable member.

FIG. 10 demonstrates the application and positioning of bridge member 80 on deformable member 10. As depicted, indentation 85 is positioned on surface 13 so that surface 13 is pressed against bed 90. In addition, sides 15 and 16 are pressed against sides 88 and 89. In short, deformable member 10 is snuggly placed in indentation 85. To prevent bridge 80 from coming in contact with wound 3, height of sides 88 and 89 are much less than the height of sides 15 and 16, and preferably half.

Bridge member 80 does not need any adhesive on surface 84. Adhesive may be applied to surface 83 to further secure it to dressing 5. Adhesive may also be applied to surface 84. FIG. 11 depicts how bridges 60 and 70 are used in conjunction with deformable member 10 and for wound 3.

FIG. 12 demonstrates that the deformable member may be cut into several equal or varying desirable lengths, instead of one length surrounding the wound area. Such application may be useful for areas on which positioning of dressings is difficult, e.g., the elbow and knee. FIG. 12 also demonstrates the versatility of application of the present invention, as it could be used in conjunction with manifold dressings, including currently available non-contact dressings. As discussed above, FIG. 12 also demonstrates the usefulness of the present invention in relieving pressure from pressure ulcers.

Figure 13:
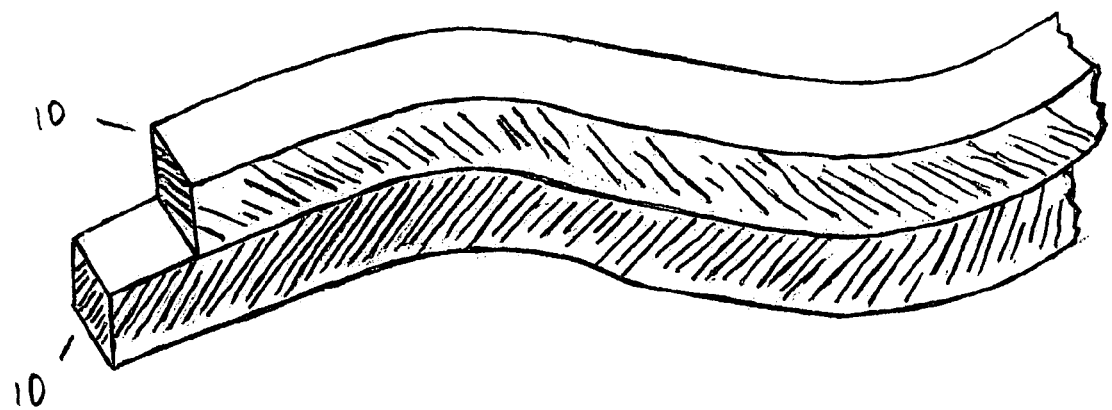
FIG. 13 depicts the deformable member of the present invention in stacked formation.

FIG. 13 depicts the stacked assembly of the deformable member of the present invention, wherein a second deformable member is positioned on the upper surface of a first deformable member. This embodiment may be used in certain situations where a greater protective height around the wound is preferable. The stacked assembly may comprise more than two deformable members. Regardless of whether it is used in stacked formation, the thinness of the deformable member of the present invention is an important consideration for practicability and patient convenience.

Figure 14A:
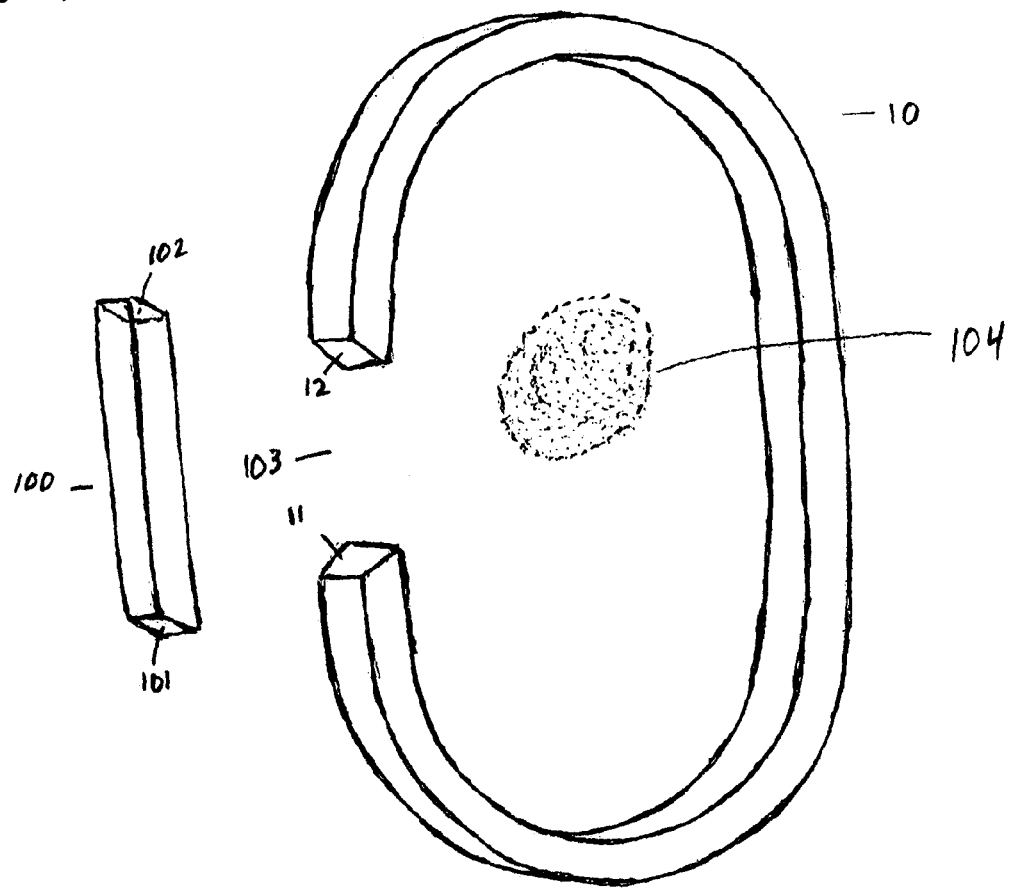
FIGS. 14A and 14B depict a connector member used in conjunction with the deformable member.
Figure 14B:
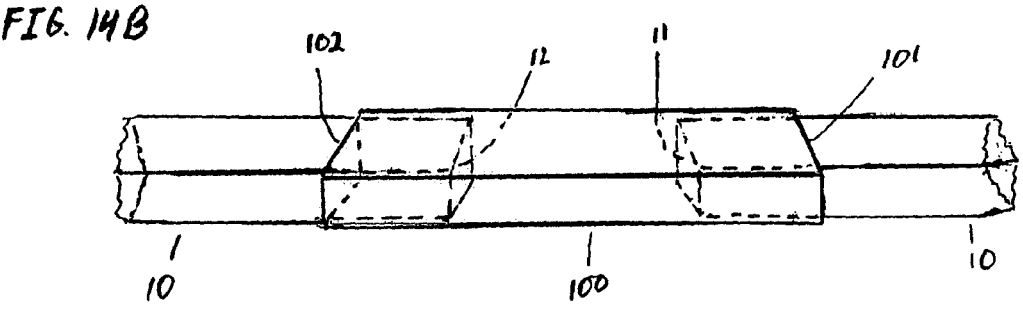

FIGS. 14A and 14B depict the connector member of the present invention and its method of application. A connector member 100 is depicted to keep deformable member 10 wrapped around wound 104. Connector member 100 may be used in circumstances where it is desirable not to apply any adhesive to either surfaces of deformable member 10. Lack of adhesive provides the opportunity for start 11 and end 12 to move away from one another and create an opening 103, as depicted in FIG. 14A. As can be appreciated, exudate from the wound, if any, can diffuse away from wound 104 through opening 103 and onto other body surface.

As depicted in FIG. 14B, connector member 100 closes opening 103 by indirectly connecting start 11 and end 12. Connector member 100 is essentially a hollow body, which may be constructed from various materials available in the industry, including those used for construction of deformable member 10. Interior perimeters of start 101 and end 102 are designed to be slightly larger than that of exterior perimeters of start 11 and end 12 of deformable member 10, allowing deformable member 10 to be inserted into connector member 100. Start 11 is inserted into start 101, and end 12 is inserted into end 102. Interior perimeter of connector member 100 should be sufficiently small to keep start 11 and end 12 in position within it. Connector member 100 can also connect two deformable members. In such circumstance, as depicted in FIG. 14B, deformable member 10 with start 11 inserted into connector member 100 is a separate deformable member than deformable member 10 with end 102 inserted into connector member 100.

As briefly discussed above, in circumstances where adhesive is not applied, deformable member 10 is held in position and around the wound by sufficient and proper pressure applied from the dressing, which may be wrapped around the body, e.g., around a limb or abdomen, or attached to the body via adhesive. The method by which the dressing is attached to the body, however, is immaterial for the purpose of the present invention.

FIGS. 15A, 15B and 15C depict various storage and dispensing apparatuses for the deformable member of the present invention. FIG. 15A shows dispenser box 200 in which the forms a coil 202 that is wound around a reel 201. Segment 203 is a portion of coil 202 that is led to outlet 204. It can be pulled out from outlet 204 and cut to a desired length with scissors, or via a blade positioned at the upper or lower lip of outlet 204.

FIG. 15B demonstrates that dispenser 210 may have several outlets 214, 215 and 216, allowing it to contain several coils. The number of coils or outlets contained in dispenser 210 are examples provided for discussion purposes only and should not be viewed as a limitation. FIG. 15B merely represents that more than one coil and more than one outlet may be used. FIG. 15C depicts an alternative dispenser 220, which does not comprise a box as in dispensers 200 and 210.

The drawings and descriptions disclosed here manifest that the present invention is deformable to conform to specific wound size and contour for protecting the wound from injurious contacts, including injury caused by adherence of dressing to wound. While the description contained herein contains many specificities, they should not be construed as limitations on the scope of the present invention, but rather as exemplifications of its preferred embodiments. Many other variations are possible. For example, the present invention may be used in wound management, post surgery and other medical applications on animals as well as humans. Clearly, the other embodiments and modifications of the present invention will occur readily to those of ordinary skill in the art in view of these teachings. Accordingly, the scope of the present invention is to be limited only by the following claims, which include all such embodiments and modifications when viewed in conjunction with the above specification and accompanying drawing.

The invention claimed is:

1. A method of protecting a wound having an irregular perimeter, the method comprising:

providing a deformable elongated strip of exudate-absorbing material, the strip having first and second ends, a length, a lower surface, an upper surface, and a layer of adhesive disposed on the lower surface;

flexing the strip along its length to conform to the irregular perimeter so as to circumscribe the wound;

adhering the lower surface of the strip along the irregular perimeter of the wound via the layer of adhesive;

after adhering the lower surface of the strip along the irregular perimeter of the wound, applying a moisture permeable layer across the wound and the upper surface of the strip;

absorbing exudate from the wound with the strip; and releasing moisture from exudate absorbed by the strip through the moisture permeable layer, wherein the moisture permeable layer is configured to absorb exudate from the wound.

2. The method according to claim 1 further comprising:
securing the moisture permeable layer using an adhesive.

3. The method according to claim 1 further comprising:
coupling at least one bridge member to the strip.

4. The method according to claim 1 further comprising:
coupling the first and second ends of the strip with a connector.

5. The method of claim 1, wherein the strip comprises a plurality of grooves to enhance flexibility.

6. The method of claim 1, wherein the strip comprises polyurethane foam.

7. Apparatus for protecting a wound having an irregular perimeter, the apparatus comprising:

a deformable elongated strip of exudate-absorbing material, the strip having first and second ends, a lower surface, an upper surface and a length, the strip adapted to flex along its length to circumscribe the wound; and an adhesive layer disposed on the lower surface of the strip, the adhesive layer configured to adhere the strip along the irregular perimeter of the wound; and a moisture permeable layer configured to be disposed across the wound and the upper surface of the strip, the moisture permeable layer configured to release moisture absorbed by the strip, wherein the moisture permeable layer is configured to absorb exudate from the wound.

8. The apparatus of claim 7, wherein the upper surface of the strip is configured to suspend the moisture permeable layer above the wound.

9. The apparatus of claim 7, wherein an adhesive layer is disposed on the upper surface of the strip.

10. The apparatus of claim 7, wherein the strip comprises at least one groove to enhance flexibility.

11. The apparatus of claim 7 further comprising at least one bridge member adapted to be coupled to the strip.

12. The apparatus of claim 7 further comprising at least one connector adapted to be coupled to at least one of the first and second ends of the strip.

13. The apparatus of claim 7, wherein the strip comprises first and second strips, wherein the second strip is secured on the upper surface of the first strip.

14. The apparatus of claim 7, wherein the length of the strip is adjustable.

15. Apparatus for protecting a wound having an irregular perimeter, the apparatus comprising:

a deformable elongated strip of exudate-absorbing material, the strip having first and second ends, a lower surface, an upper surface and a length, the strip adapted to flex along its length to circumscribe the wound; and an adhesive layer disposed on the lower surface of the strip, the adhesive layer configured to adhere the strip along the irregular perimeter of the wound; and a moisture permeable layer configured to be disposed across the wound and the upper surface of the strip, the moisture permeable layer configured to release moisture absorbed by the strip, wherein the strip comprises first and second strips, wherein the second strip is secured on the upper surface of the first strip.

* * * * *